United States Patent [19]

Sparks

[11] Patent Number: 5,505,962
[45] Date of Patent: Apr. 9, 1996

[54] CONTROLLED RELEASE PHARMACEUTICAL FORMULATION

[75] Inventor: Randall T. Sparks, Gainesville, Ga.

[73] Assignee: Elan Corporation, plc, Athlone, Israel

[21] Appl. No.: 307,392

[22] Filed: Sep. 16, 1994

Related U.S. Application Data

[63] Continuation of Ser. No. 995,355, Dec. 22, 1992, abandoned, which is a continuation of Ser. No. 714,974, Jun. 13, 1991, abandoned, which is a continuation of Ser. No. 357,521, May 26, 1989, abandoned.

[30] Foreign Application Priority Data

May 27, 1988 [IL] Israel ......................................... 1616/88

[51] Int. Cl.$^6$ ................................ A61K 9/22; A61K 9/28; A61K 9/32
[52] U.S. Cl. ................ 424/473; 424/474; 424/479; 424/480; 424/481; 424/482; 424/679
[58] Field of Search ......................................... 424/473, 474, 424/479, 480, 481, 482, 679

[56] References Cited

U.S. PATENT DOCUMENTS

| | | | |
|---|---|---|---|
| 3,538,214 | 11/1970 | Polli et al. | 424/19 |
| 4,140,756 | 2/1979 | Gallian | 424/21 |
| 4,629,620 | 12/1986 | Lindahl et al. | 424/15 |
| 4,784,858 | 11/1988 | Ventouras | 424/468 |

FOREIGN PATENT DOCUMENTS

| | | | |
|---|---|---|---|
| 900824 | 2/1986 | Belgium. | |
| 0171457 | 8/1984 | European Pat. Off. | A61K 9/24 |
| 0211991 | 8/1985 | European Pat. Off. | A61K 9/32 |
| 0224146 | 6/1987 | European Pat. Off. | A61K 9/24 |

*Primary Examiner*—Gollamudi S. Kishore
*Attorney, Agent, or Firm*—Mary L. Severson

[57] ABSTRACT

An improved controlled release tablet formulation for the release of potassium chloride through a differentially permeable membrane from which the release of potassium chloride can be accurately controlled to minimize the likelihood of producing high localized concentrations of potassium within the gastrointestinal tract.

10 Claims, No Drawings

CONTROLLED RELEASE PHARMACEUTICAL FORMULATION

This application is a continuation of application Ser. No. 07/995,355, filed Dec. 22, 1992, now abandoned which is a continuation of Ser. No. 07/714,974, filed Jun. 13, 1991, now abandoned, which is a continuation of Ser. No. 07/357,521, filed May 26, 1989, now abandoned.

FIELD OF INVENTION

This invention relates to controlled release pharmaceutical formulations and, in particular, to a controlled release tablet formulation for the release of potassium chloride through a differentially permeable membrane.

BACKGROUND OF THE INVENTION

Potassium ion is the principal intracellular cation of most body tissues. Potassium ions participate in a number of essential physiological processes, including the maintenance of intracellular tonicity, the transmission of nerve impulses, the contraction of cardiac, skeletal, and smooth muscle and the maintenance of normal renal function.

Potassium depletion may occur whenever the rate of potassium loss through renal excretion and/or loss from the gastrointestinal tract exceeds the rate of potassium intake. Such depletion usually develops slowly as a consequence of prolonged therapy with oral diuretics, primary or secondary hyperaldosteronism, diabetic ketoacidosis, severe diarrhea, or inadequate replacement of potassium in patients on prolonged parenteral nutrition. Potassium depletion due to these causes is usually accompanied by a concomitant deficiency of chloride and is manifested by hypokalemia and metabolic alkalosis. Potassium depletion may produce weakness, fatigue, disturbances of cardiac rhythm (primarily ectopic beats), prominent U-waves in the electrocardiogram, and in advanced cases flaccid paralysis and/or impaired ability to concentrate urine.

Potassium depletion associated with metabolic alkalosis is managed by correcting the fundamental causes of deficiency whenever possible and administering supplemental potassium chloride, in the form of high potassium food or potassium chloride solution, tablets or capsules.

Potassium chloride is conventionally administered in the form of tablets or capsules by the oral route. These dosage forms have the advantages of convenience and ease of administration. It is desired in potassium replacement therapy that the total body potassium level be restored to normal quickly and, for patient convenience, it is desirable that the normal level be sustained for a significant period of time.

The usual dietary intake of potassium by the average adult is 40 to 80 mEq per day. Potassium depletion sufficient to cause hypokalemia usually requires the loss of 200 mEq or more of potassium from the total body store. Dosage must be adjusted to the individual needs of each patient but is typically in the range of 20 mEq per day for the prevention of hypokalemia and 40–100 mEq or more per day for the treatment of potassium depletion.

Potassium chloride, however, is a known gastrointestinal tract irritant, the most common adverse reactions to oral administration being nausea, vomiting, abdominal discomfort and diarrhea. Also, the administration of potassium salts, particularly in enteric-coated tablets, may cause intestinal ulceration, sometimes with hemorrhage and perforation or with the late formation of strictures. These symptoms are best prevented by either diluting a liquid preparation to a concentration that can be tolerated by the patient or providing a controlled release formulation to minimize the likelihood of producing high localized concentrations of potassium within the gastrointestinal tract. A second major problem associated with the administration of potassium chloride, even dilute liquid preparations thereof, is patient noncompliance due to the unpalatable taste of the liquid preparations.

Several controlled release tablet formulations for potassium chloride and other active ingredients are known in the art. For example, U.S. Pat. No. 3,538,214 discloses a controlled release formulation comprising a tablet core containing potassium chloride coated with a film of water-insoluble plastic and a film modifying material that is selectively soluble in either the stomach or intestinal fluids so that a membranous or dialytic type film remains when the film modifying material is dissolved in the gastrointestinal tract permitting the potassium chloride to leach out slowly. Also known is a slow release formulation in which a conventional tablet is encased in an impermeable membrane provided with a single aperture through which the active ingredient exits following administration to a patient. The release of active ingredient from the latter tablet formulation is determined by the rate of release of active ingredient from the aperture. Additionally, controlled release tablet formulations exist which are known as matrix tablets and which consist of polymeric material having an active ingredient dispersed therethrough. In use, the active ingredient diffuses out of the polymer matrix and the formulation ultimately breaks up completely.

Gastric irritation and gastric and intestinal ulcerations, however, have been reported following the use of several of the above sustained release formulations when the active ingredient is potassium chloride. It is believed that such formulations produce high concentrations of potassium that are localized within the gastrointestinal tract.

As discussed above, potassium chloride replacement therapy requires large dosages of potassium chloride, therefore it is desirable to produce a tablet wherein at least 80% of the total weight of the tablet is potassium chloride, otherwise the size of the tablet is increased to where it becomes difficult to swallow. Furthermore, it is also desirable to impart a sufficient degree of hardness to the tablet core without increasing the friability.

One of the disadvantages with the slow release formulation of U.S. Pat. No. 3,538,214 is that the maximum weight percent of potassium chloride per total weight of tablet is only 49%.

Belgium Pat. No. 900,824, granted October 31, 1984 in the name of the assignee of the present application, discloses a controlled release formulation for the release of chloride through a differentially permeable membrane. The potassium chloride formulation disclosed therein, however, is for a tablet where the potassium chloride is about 66% of the total tablet weight.

SUMMARY OF THE INVENTION

Therefore, it is an object of the present invention to provide an improved controlled release tablet formulation from which the release of potassium chloride can be accurately controlled so as to ensure a predetermined rate of release of potassium chloride to minimize the likelihood of producing high localized concentrations of potassium within the gastrointestinal tract.

A further object is to provide an improved potassium chloride slow release formulation wherein the % weight of potassium chloride can be increased without substantially increasing tablet size.

And yet another object of the present invention is to provide a tablet core having sufficient hardness to withstand the coating process without increasing the friability.

Briefly, the foregoing objects are accomplished by providing a controlled release formulation comprising a tablet core containing potassium chloride and a differentially permeable membrane surrounding the core, said membrane including a potassium chloride permeable, water soluble component and a potassium chloride impermeable, water insoluble component which is optionally water permeable, wherein the water soluble component dissolves when the tablet is placed in an aqueous environment and results in the generation of pores which permit the egress of potassium chloride and any excipients that are present from the core at a rate allowing controlled release thereof.

According to the invention there is provided a controlled release potassium chloride containing tablet formulation for oral administration which does not irritate the gastric mucosa, said tablet comprising: a core of potassium chloride in association with a pharmaceutically acceptable excipient; and a differentially permeable membrane surrounding the core containing a potassium chloride impermeable component and a potassium chloride permeable component which is water soluble and dissolves in water to generate pores in the membrane to permit the egress of the potassium chloride from the core in an aqueous environment, the ratio of the potassium chloride impermeable component to potassium chloride permeable component being effective to permit release of potassium chloride at a rate which does not irritate the gastric mucosa, said rate being measured in vitro as a dissolution rate which when measured according to U.S. Pharmacopoeia 21 paddle method using water substantially corresponds to the following dissolution profile:

(a) from 15 to 35% of the total potassium chloride is released after 1 hour of measurement;

(b) from 40 to 60% of the total potassium chloride is released after 2 hours of measurement;

(c) from 65–85% of the total potassium chloride is released after 3 hours of measurement; and (d) not less than 85% of the total potassium chloride is released after 8 hours of measurement, the potassium chloride component of the tablet being present in an amount of at least 80% by weight of the tablet.

DETAILED DESCRIPTION OF THE INVENTION

According to a preferred embodiment of the present invention, a controlled release tablet formulation is provided comprising a tablet core containing the active ingredient, potassium chloride, in association with a pharmaceutically acceptable excipient and a differentially permeable membrane surrounding the core, said membrane including one component being water soluble and permeable to said potassium chloride and another component being water insoluble and impermeable to said potassium chloride.

Preferably, the tablet core has the following properties:

i) a rapid dissolution rate when tested by the method of U.S. Pharmacopoeia 21, namely a T90% (time to 90%) dissolution of not more than 30 minutes;

ii) sufficient hardness to withstand the coating process used to form the differentially permeable membrane as hereinafter described;

iii) a convex shape to avoid sticking during the coating process; and iv) includes one or more highly soluble ingredients to create a flow of liquid out of the tablet core in an aqueous environment.

The tablet core is preferably produced by a wet granulation technique to permit a higher weight % of potassium chloride per tablet without compromising the desired degree of hardness. The preferred degree of hardness is greater than 6 kp with a preferred friability of less than 1%.

The differentially permeable membrane is generally between 1 and 20% weight of the total weight of the tablet. Preferably the weight of the differentially permeable membrane is from about 3% to about 15% of the total weight of the tablet.

The drug impermeable component of the membrane is water insoluble, but optionally water permeable.

The drug permeable component of the membrane is a water soluble component which dissolves in water resulting in the generation of pores which permit the egress of the potassium chloride and excipient(s) from the core in an aqueous environment.

Alternatively, the drug permeable component may be permeable to both water and the active ingredient and associated excipient(s). The drug permeable component may also be porous.

Preferred materials for the potassium chloride impermeable component of the membrane are: ethylcellulose, polyvinylchloride, methylcellulose, polyurethane, cellulose acetate, polycarbonate, polyethylene, polypropylene, shellac and polymers of acrylic and methacrylic acids and esters thereof such as EUDRAGIT RS (EUDRAGIT RS is a Trade Mark). An especially preferred potassium chloride impermeable component is ethylcellulose.

Preferred materials for the potassium chloride permeable component of the membrane are: polyvinyl alcohol, polyvinylpyrrolidone (PVP) such as pharmaceutical grade PVP sold under the Trade Mark POVIDONE, polymers of acrylic and methacrylic acid and esters thereof such as EUDRAGIT RL ( EUDRAGIT RL is a Trade Mark), and EUDRAGIT E ( EUDRAGIT E is a Trade Mark ), fumaric acid, citric acid, tartaric acid, sodium citrate, sodium bicarbonate, sodium fumarate, sodium carbonate, monosaccharides and disaccharides and hydroxypropylmethyl cellulose. An especially preferred potassium chloride permeable component is polyvinylpyrrolidone. An especially suitable monosaccharide is glucose.

More specifically, EUDRAGIT polymers are polymeric lacquer substances based on acrylate s and/or methacrylates. EUDRAGIT RS and RL are acrylic resins comprising copolymers of acrylic and methacrylic acid esters with a low content of quaternary ammonium groups and are described in the "EUDRAGIT" brochure of Mssrs. Rohm and Haas (1985) wherein detailed physical-chemical data of these products are given. EUDRAGIT E is described in the "EUDRAGIT E" brochure of Messrs. Rohm Pharma GmbH (1986).

The differentially permeable membrane is preferably formed by dissolving at least one potassium chloride permeable component and at least one potassium chloride impermeable component in a respectively suitable solvent at a concentration which allows spraying with an air spray or airless spray system in a conventional manner. Preferably, the concentration of each component used varies between 5% and 90% of the total weight of the membrane depending on the material involved and the viscosity of the resulting solution.

Each solution of each membrane component or mixtures of membrane components may include one or more additives which facilitate spraying such as plasticizers or other additives such as coloring agents and opacifiers. These additives, however, do not substantially affect the nature of the membrane formed.

Preferred materials for a plasticizer component of the membrane are: propylene glycol, glycerin, polyethylene glycol, triacetin, triethyl citrate, tributyl citrate, dibutyl sebacate, diethyl phthalate, castor oil, mineral oil and acetylated monoglycerides. An especially preferred plasticizer component is propylene glycol.

The final solution used in coating the tablet cores is made by mixing the solutions of soluble/permeable component(s) and the insoluble/impermeable component(s) so that the proportion of soluble to insoluble component (s) is between 1:9 and 9:1 with a preferred ratio range between 2:7 and 3:2. In addition to plasticizers, pigments, and coloring agents, other conventional additives may also be added to the final solution. The amount of plasticizer in the final coating solution is between 5–30% weight of the final coating solution with a preferred range of about 10–20%.

Preferably, the membrane is formed around the tablet core by spraying using either an air spray or an airless spray system and standard tablet coating equipment. As stated above, the differentially permeable membrane preferably increases the weight gain per tablet by about 3–15%. After spraying, the coated tablets are oven dried at 40°–50° C. to evaporate all residual solvents.

The membrane coated tablets have a dissolution rate which is determined by the solubility properties of the potassium chloride and excipient(s) in the core tablet and by the composition of the membrane. The rate of dissolution of the potassium chloride is substantially independent of the pH of the surrounding milieu.

Potassium chloride tablets made according to the present invention are very compact requiring as little as 10% added excipients to achieve the desired sustained release. It is generally preferred that the tablet core dimensions do not exceed 9.61 mm for the short axis, 15.38 mm for the long axis and 6.97 mm in thickness.

When tested by the paddle method of the U.S. Pharmacopoeia 21 using water as the medium, it was found that:

(a) from 15 to 35% of the total potassium chloride is released after 1 hour of measurement;

(b) from 40 to 60% of the total potassium chloride is released after 2 hours of measurement;

(c) from 65–85% of the total potassium chloride is released after 3 hours of measurement; and (d) not less than 85% of the total potassium chloride is released after 8 hours of measurement.

Bioavailability studies were conducted to determine the preferred rates of dissolution and that the formulations were bioequivalent to known sustained or controlled release formulations of potassium chloride.

Dosage, of course, must be adjusted to the individual patient, but typically about 1500 mg (20 mEq) per day is required for the prevention of hypokalemia and about 3000–7500 mg (40–100 mEq) per day is required for the treatment of potassium depletion. Tablet formulations according to the present invention may contain potassium chloride in the range of 200 mg to 1500 mg per tablet. An especially preferred range is from 600 mg to 1125 mg of potassium chloride per tablet.

Potassium chloride tablet formulations substantially free of gastric irritant properties were prepared according to the following examples which are intended for illustrative purposes only.

EXAMPLE 1

Potassium chloride tablet cores were prepared by milling 144 kg potassium chloride using conventional milling equipment to reduce the average particle size to below No. 60 mesh. The milled potassium chloride was combined with sufficient 11.11% (weight/weight) povidone dissolved in Specially Denatured Alcohol, formula 3a, (SD3A) anhydrous to form a proper wet granulation. The wet granulation was spread out in a layer of approximately 1 inch thick, on paper lined trays and oven dried for 10 hours at 40°–50° C.

The dry granules were passed either through an oscillating granulator fitted first with a No. 4 mesh screen and secondly with a No. 16 mesh screen or through a fitzmill granulator with the knives set forward at medium speed. Approximately 2 kg of the dry granules were removed and hand mixed with 0.72 kg of magnesium stearate and then combined with the remaining dry granules in a suitable blender, such as a 20 cubic ft. Patterson Kelly crossflow blender. The material was blended for 5 minutes and discharged into double polyethylene lined containers.

The granule blend was compressed into oval tablets at a weight of 619 mg calculated to yield 600 mg (8mEq) of potassium chloride per tablet. The tablet press used was a conventional rotary type having plain oval punch tips with dimensions of about 0.33–0.75 inches for the long axis and about 0.25–0.45 inches for the short axis. The tablet cores were then placed into a suitable coating pan for application of the differentially permeable membrane.

The membrane solution was prepared by mixing the following ingredients in the amounts stated:

4.5% (wt/wt) ethylcellulose 5.882 kg 2.5% (wt/wt) povidone 3.213 kg 1.2% (wt/wt) propylene glycol 1.602 kg (plasticizer)

91.8% (wt/wt) SD3-A 119.303 kg

The membrane solution was applied to the tablet cores in an ACCELA-COTA (ACCELA-COTA is a Trademark) coating machine (Manesty Machines Limited) using a conventional spray system until a % weight increase of 10 7.3% was achieved. Alternatively, the membrane solution could be applied to the tablet cores in a coating pan that supplies a constant volume of heated air through the tablet bed while monitoring both the incoming and outgoing air temperature. The tablets were then spread on paperlined trays and oven-dried at 40°–50° C. for 8 hours.

EXAMPLE 2

Example 1 was repeated except the membrane solution was applied to the tablet core until a 4.0% weight increase was achieved.

EXAMPLE 3

Example 1 was repeated except the membrane solution was applied to the tablet core until a 10.6% weight increase was achieved.

EXAMPLE 4

Example 1 was repeated except the membrane solution was applied to the tablet core until a 13.3% weight increase was achieved.

When Examples 1–4 were tested by the U.S. Pharmacopoeia 21 paddle method using water as the medium, the dissolution rate was found to decrease as the amount of membrane applied to the tablet core increased. The dissolution rates were found to correspond to the % weight of membrane as follows:

| Time (h) | 4.0% Wt | 7.3% Wt | 10.6% Wt | 13.3% Wt |
|---|---|---|---|---|
| 1 | 33.4 | 28.0 | 26.0 | 18.7 |
| 2 | 60.0 | 61.5 | 54.0 | 46.2 |
| 4 | — | — | 96.4 | 98.7 |

The potassium chloride formulations tested above were prepared by coating the tablets in 10.0 kg. increments in a 30 inch conventional coating pan using an airless spray system. The percent weight increase of the tablets was calculated by taking the weight difference between the average starting weight of a sample of 100 tablets and the average weight of a sample of 100 tablets after coating.

EXAMPLES 5–9

In a second dissolution study, the potassium chloride tablets were coated in 150.0 kg increments having % weight increases of 2.1%, 5.6%, 6.75%, 6.95%, and 7.4% (Examples 5–9). All remaining parameters were held constant as defined in Example 1. The % weight increase was calculated by the same procedure described for coating the tablets in 10.0 kg increments. The dissolution rates were found to be as follows:

| Time (h) | 2.1% Wt | 5.6% Wt | 6.75% Wt | 6.95% Wt | 7.4% Wt |
|---|---|---|---|---|---|
| 1 | 59.9 | 32.5 | 30.1 | 30.5 | 21.7 |
| 2 | 81.1 | 59.7 | 56.6 | 55.8 | 50.0 |
| 3 | 94.0 | 78.0 | 75.0 | 74.0 | 72.0 |
| 4 | 108.0 | 92.8 | 96.9 | 92.2 | 91.0 |

In addition to increasing the % weight of the differentially permeable membrane, the dissolution rates may be controlled by varying the ratio of the potassium chloride permeable, water soluble component to the potassium chloride impermeable, water insoluble component to plasticizer as illustrated in the following Examples.

EXAMPLE 10

Tablet cores were prepared according to Example 1 except that the milled potassium chloride was combined with sufficient 18% (weight/weight) povidone dissolved in anhydrous SD3-A to form a proper wet granulation.

The membrane solution was prepared by mixing the following ingredients in the amounts stated:

| | |
|---|---|
| 4.5% (wt/wt) ethylcellulose | 5.899 kg |
| 2.5% (wt/wt) povidone | 3.196 kg |
| 1.2% (wt/wt) propylene glycol (plasticizer) | 1.599 kg |
| 91.8% (wt/wt) SD3-A | 119.302 kg |

The membrane solution was applied according to Example 1.

The dissolution rate was determined to be as follows:

| Time (h) | % Release |
|---|---|
| 1 | 24.9 |
| 2 | 48.7 |
| 3 | 74.5 |
| 6 | 103.0 |

EXAMPLE 11

Potassium chloride tablets were prepared according to Example 10 except that the wet granulation for the tablet cores was formed using milled potassium chloride combined with sufficient 13% (weight/weight) povidone dissolved in anhydrous SD3-A.

The dissolution rate was determined to be as follows:

| Time (h) | % Release |
|---|---|
| 1 | 26.0 |
| 2 | 54.0 |
| 4 | 91.4 |
| 6 | 98.6 |

The dissolution % values reported above for Examples 10 and 11 represent an average of six separate analyses performed on potassium chloride tablet formulations prepared according to Example 10 and Example 11, respectively.

The control of potassium chloride dissolution from the tablet core through the differentially permeable membrane can also be achieved by varying the surface to volume ratio of the tablet by varying the size of the tablet. As the size of the tablet is increased, the dissolution rate of potassium chloride decreases. While variation of the tablet size can be used to alter the dissolution profile, it is generally not the preferred route because tablet size has certain defined acceptable limits. Moreover, the dissolution of potassium chloride can be controlled more effectively by altering the characteristics of the membrane.

Dissolution of potassium chloride can also be controlled by varying the amount of potassium chloride present in the tablet core. As indicated above the preferred weight % of potassium chloride per weight of tablet is approximately 90%. The concentration of potassium chloride can range from 200 mg to 1500 mg with the preferred range being from 600 mg to 1125 mg. Increasing the concentration of potassium chloride in the core results in an increased dissolution rate, provided that all other parameters remain constant.

The invention is not intended to be limited to the embodiments described above, which may be modified and/or varied without departing from the scope of the invention.

What is claimed is:

1. A controlled release potassium chloride containing tablet formulation for oral administration which does not irritate the gastric mucosa, said tablet consisting essentially of: a core of potassium chloride in association with a pharmaceutically acceptable excipient, wherein said pharmaceutically acceptable excipient is selected from group consisting of lactose, talc, microcrystalline cellulose, stearic acid, magnesium stearate sodium stearate and polyvinylpyrrolidone or a mixture thereof, said core of said tablet having a rapid dissolution rate when tested by the method of U.S. Pharmacopoeia 21, namely a T90% (time to 90%) dissolution of not more than thirty minutes; and a differentially permeable membrane surrounding said core containing a potassium chloride impermeable component selected from group consisting of ethylcellulose, polyvinylchloride, methylcellulose, polyurethane, cellulose acetate, polycarbonate, polyethylene, polypropylene, shellac and polymers of acrylic and methacrylic acids and esters thereof and a potassium chloride permeable component which is water soluble and dissolves in water to generate pores in said membrane to permit the egress of the potassium chloride from said core in an aqueous environment selected from the group consisting of polyvinyl alcohol, polyvinylpyrrolidone, fumaric acid, citric acid, tartaric acid, sodium citrate, sodium bicarbonate, sodium fumarate, sodium carbonate, monosaccharides and disaccharides, hydroxypropylmethylcellulose and polymers of acrylic and methacrylic acids and esters thereof, the ratio of the potassium chloride impermeable component to potassium chloride permeable component in the range of about 1:9 to 9:1 being effective to permit release of potassium chloride from said tablet at a rate which does not irritate the gastric mucosa, said rate being measured in vitro as a dissolution rate which when measured according to U.S. Pharmacopoeia 21 paddle method using water substantially corresponds to the following dissolution profile:

(a) from 15 to 35% of the total potassium chloride is released after 1 hour of measurement;

(b) from 40 to 60% of the total potassium chloride is released after 2 hours of measurement;

(c) from 65 to 85% of the total potassium chloride is released after 3 hours of measurement; and (d) not less than 85% of the total potassium chloride is released after 8 hours of measurement, the potassium chloride component of said tablet being present in an amount of at least 80% by weight of the tablet.

2. A controlled release potassium chloride containing tablet formulation for oral administration which does not irritate the gastric mucosa, said tablet consisting essentially of a core of potassium chloride in association with a pharmaceutically acceptable excipient, where, in said pharmaceutically acceptable excipient is selected from the group consisting of lactose, talc, microcrystalline cellulose, stearic acid, magnesium stearate, sodium stearate and polyvinylpyrrolidone or a mixture thereof, said core of aid tablet having rapid dissolution rats when tested by the method of U.S. Pharmacopoeia 21, namely a T90% (time to 90%) dissolution of not more than thirty minutes; and a differentially permeable membrane surrounding the core containing a potassium chloride impermeable component selected from group consisting of ethylcellulose, polyvinylchloride, methylcellulose, polyurethane, cellulose acetate, polycarbonate, polyethylene, polypropylene, shellac and polymers of acrylic and methacrylic acids and esters thereof and a potassium chloride permeable component which is water soluble and dissolves in water to generate pores in the membrane to permit the egress of the potassium chloride from the core in an aqueous environment selected from the group consisting of polyvinyl alcohol, polyvinylpyrrolidone, fumaric acid, citric acid, tartaric acid, sodium citrate, sodium bicarbonate, sodium fumarate, sodium carbonate, monosaccharides and disaccharides, hydroxypropylmethylcellulose and polymers of acrylic and methacrylic acids and esters thereof and a plasticizer selected from the group consisting of propylene glycol, glycerin, polyethylene glycol, triacetin, triethyl citrate, tributyl citrate, dibutyl sebacate, diethyl phthalate, castor oil, mineral oil and acetylated monoglycerides, the ratio of the potassium chloride impermeable component to potassium chloride permeable component in the range of about 1:9 to 9:1 being effective to permit release of potassium chloride from said tablet at a rate which does not irritate the gastric mucosa, said rate being measured in vitro as a dissolution rate which when measured according to U.S. Pharmacopoeia 21 paddle method using water substantially corresponds to the following dissolution profile:

(a) from 15 to 35% of the total potassium chloride is released after 1 hour of measurement;

(b) from 40 to 60% of the total potassium chloride is released after 2 hours of measurement;

(c) from 65 to 85% of the total potassium chloride is released after 3 hours of measurement; and (d) not less than 85% of the total potassium chloride is released after 8 hours of measurement, the potassium chloride component of the tablet being present in an amount of at least 80% by weight of the tablet.

3. The tablet formulation according to claim 2, wherein the plasticizer is propylene glycol.

4. The tablet formulation according to claim 1 wherein the ratio of potassium chloride, impermeable to permeable components in the membrane is in the range of about 2:3 to 7:2.

5. The tablet formulation according to claim 1, wherein the potassium chloride impermeable component is ethylcellulose.

6. The tablet formulation according to claim 1, wherein the potassium chloride permeable component is polyvinylpyrrolidone. polyethylene glycol, triacetin, triethyl citrate, tributyl citrate, dibutyl sebacate, diethyl phthalate, castor oil, mineral oil and acetylated monoglycerides.

7. The tablet formulation according to claim 1, wherein the potassium chloride impermeable component is permeable to water but water insoluble.

8. The tablet formulation according to claim 1, wherein the potassium chloride constitutes approximately 90% of the total weight of the tablet.

9. The tablet formulation according to claim 1, wherein the degree of hardness of the tablet core is greater than 6 kp.

10. The tablet formulation according to claim 9, wherein the friability is less than 1%.

* * * * *